United States Patent [19]

Celmer et al.

[11] Patent Number: 4,652,523
[45] Date of Patent: Mar. 24, 1987

[54] METHOD OF PREPARING A NEW POLYETHER ANTIBIOTIC FROM STREPTOMYCES

[75] Inventors: Walter D. Celmer, New London; Walter P. Cullen, East Lyme, both of Conn.; Hiroshi Maeda, Aichi; Junsuke Tone, Chita, both of Japan

[73] Assignee: Pfizer Inc., New York, N.Y.

[21] Appl. No.: 660,619

[22] Filed: Oct. 15, 1984

Related U.S. Application Data

[62] Division of Ser. No. 549,378, Nov. 7, 1983, Pat. No. 4,547,523.

[51] Int. Cl.$^4$ ............... C12P 17/18; C12R 1/465
[52] U.S. Cl. .................................. 435/119; 435/886
[58] Field of Search .............. 435/119, 170, 253, 886; 548/217; 514/375

[56] References Cited

U.S. PATENT DOCUMENTS 3,923,823 12/1975 Gale et al. ........................... 548/217
4,352,934 10/1982 Liu et al. ............................ 548/217

Primary Examiner—Thomas G. Wiseman
Assistant Examiner—Elizabeth C. Weimar
Attorney, Agent, or Firm—Charles J. Knuth; Peter C. Richardson; J. Trevor Lumb

[57] ABSTRACT

A new polyether antibiotic has been isolated from fermentations of a new microorganism of the genus Streptomyces. This new microorganism is designated as N478-13 and it has been named Streptomyces routienii Huange sp. nov., (ATCC 30446). The new antibiotic exhibits antibacterial activity against a variety of gram-positive bacteria; it can be used to control swine dysentery; and it promotes increased efficiency of feed utilization (i.e. promotes increased growth) in swine and ruminants.

1 Claim, No Drawings

METHOD OF PREPARING A NEW POLYETHER ANTIBIOTIC FROM STREPTOMYCES

This application is a division of application Ser. No. 549,378, filed Nov. 7, 1983, now U.S. Pat. No. 4,547,523.

BACKGROUND OF THE INVENTION

This invention relates to a new antibiotic substance, which has been designated CP-61,405. Said new antibiotic substance was isolated from fermentations of a new microorganism of the genus Streptomyces. The new microorganism was obtained from a soil sample found in Dazaifu, Fukuoka Prefecture, Japan and it has been assigned the code number N478-13. Chemically, the new antibiotic substance of this invention is a new member of the so-called polyether class of antibiotics, and it can be compared with Antibiotic X-14885A U.S. Pat. No. 4,352,934).

SUMMARY OF THE INVENTION

This invention provides a new antibiotic substance, designated CP-61,405, having the chemical formula

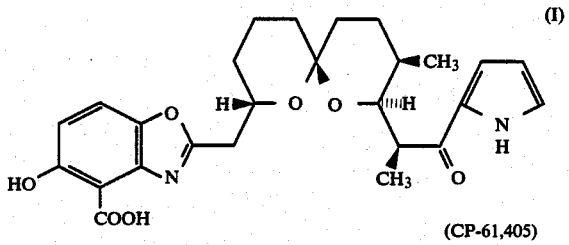

(CP-61,405)

and the pharmaceutically-acceptable base salts thereof.

The compound of formula I possesses antibacterial activity against a variety of gram-positive bacteria; it is effective in the control of swine dysentery; and it promotes increased efficiency of feed utilization (i.e. promotes growth) in swine and ruminants.

The compound of formula I has been isolated by culture of a new microorganism which has been identified as a new species of the genus Streptomyces. Said new microorganism has been designated N478-13, and it has been named *Streptomyces routienii* Huang sp. nov. It is on deposit with American Type Culture Collection under Accession No. 39446.

Also embraced within this invention are: a method of of inhibiting swine dysentery using the antibiotic of formula I or a pharmaceutically-acceptable salt thereof; a method of increasing feed utilization in poultry and ruminants using the antibiotic of formula I or a pharmaceutically-acceptable salt thereof; pharmaceutical compositions comprising the compound of formula I or a pharmaceutically-acceptable salt thereof; a method for producing the antibiotic of formula I or a pharmaceutically-acceptable salt thereof by cultivating said *Streptomyces routienii* Huang sp. nov.; and a biologically pure culture of said microorganism of the species *Streptomyces routienii* Huang sp. nov.

DETAILED DESCRIPTION OF THE INVENTION

The antibiotic substance of this invention is produced by fermentation of a new microorganism designated N478-13, which was obtained from a soil sample collected in Dazaifu, Fukuoka Prefecture, Japan. Culture N478-13 was characterized and identified by Liang H. Huang, PhD, Pfizer Inc., Groton, Conn., U.S.A. as described hereinbelow.

On examination, culture N478-13 was found to have the morphological features of a Streptomyces species. The results of whole-cell analyses provided additional evidence that culture N478-13 belongs to the genus Streptomyces.

Culture N478-13 was planted from a slant into liquid ATCC medium 172 and grown for four days at 28° C. on a shaker. It was then centrifuged for 20 minutes, washed three times with sterile, distilled water and planted on media commonly used for identification of members of the Actinomycetales. The culture was incubated at 28° C. and the results were read at various times, but most commonly at 14 or 15 days.

Identification media used for the characterization of the culture and references for their composition are as follows:

1. Tryptone-Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, The Actinomycetes, Vol. 2, medium no. 1, p. 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no. 28, p. 331.
11. Nutrient Agar—Ibid, medium no. 14, p. 330.
12. Gordon and Smith's Tyrosine Agar—R. E. Gordon and M. M. Smith, Jr. Bact. 69: 147–150, 1955.
13. Casein Agar—Ibid.
14. Calcium Malate Agar—S. A. Waksman, Bact. Rev. 21: 1–29, 1957.
15. Gelatin—R. E. Gordon and J. M. Mihm, Jr. Bact. 73: 15–27, 1957.
16. Starch—Ibid.
17. Organic Nitrate Broth—Ibid.
18. Dextrose Nitrate Broth—S. A. Waksman, The Actinomycetes, Vol. 2, medium no. 1, p. 328, 1961, with 3 g. dextrose substituted for 30 g. sucrose and agar omitted.
19. Potato Carrot Agar—M. P. Lechevalier, Jr. Lab. and Clinical Med. 71: 934–944, 1968 but use only 30 g. potatoes, 2.5 g. carrots and 20 g. agar.
20. 2% Tap Water Agar.
21. Skim Milk—Difco.
22. Cellulose utilization—
   (a) H. L. Jensen, Proc. Linn. Soc. N.S.W. 55: 231–248, 1930.
   (b) M. Levine and H. W. Schoenlein, A Compilation of Culture Media, medium no. 2511, 1930.
23. Carbohydrates—ISP #9 medium, Difco.
24. Temperature Range—ISP #2 medium plus 50 ml. of coconut milk per liter of the medium.

Culture N478-13 exhibited the following characteristics, with colors described in common terminology and also with reference to color chips from the Color Harmony Manual, fourth edition. Whole cell amino acid and sugar analyses were carried out using the methods in Becker, B. et al., *Appl. Microbiol.*, 12: 421-423, 1964; and in Lechevalier, M. P., *J. Lab. Clin. Med.*, 71: 934-944, 1968.

Yeast Extract-Malt Extract Agar—Growth good, white, pale yellow, tan to brown (2ba, 3gc, 3ie), raised, wrinkled, aerial mycelium white to pale yellow (2ba); reverse brown (3gc, 4ie); soluble pigment yellowish brown (3lc).

Oatmeal Agar—Growth moderate to good, white, cream to pale yellow (1½ca, 2ba), slightly raised, smooth, or occuring as isolated colonies, aerial mycelium white to pale yellow (2ba); reverse cream (1½ca); soluble pigment pale yellowish (1½ca).

Inorganic Salts-Starch Agar—Growth moderate, white to cream (2ca), raised, roughened to wrinkled, aerial mycelium white to pale yellow (2ba); reverse brown (4ie); soluble pigment grayish yellow (2gc).

Glycerol-Asparagine Agar—Growth poor to moderate, pale yellowish (2ca, 2ea) with white dots of aerial mycelium, slightly raised, smooth, or occurring as isolated colonies; with sparse, white to pale yellow (2ba) aerial mycelium; reverse same as surface; soluble pigment pale yellowish (1½ca).

Czapek-Sucrose Agar—Growth good, yellowish to tan (2ea, 3gc, 3ie), raised, wrinkled, no aerial mycelium; reverse yellowish brown (3ic); soluble pigment yellowish brown (3lc).

Glucose-Asparagine Agar—Growth white, cream to dark yellowish (2ca, 2lc), raised, wrinkled to smooth, or occurring as isolated colonies, aerial mycelium white; reverse dark yellowish (2lc); soluble pigment greenish yellow (1ga).

Gordon and Smith's Tyrosine Agar—Growth moderate to good, white to pale yellow (2ba), slightly raised, smooth to slightly granular; or occurring as small, isolated colonies; aerial mycelium white to pale yellow; reverse pale yellow (2ea); soluble pigment dark yellow (2lc).

Calcium Malate Agar—Growth moderate, white, cream to pale yellow (2ba), slightly to moderately raised, smooth to granular; or occurring as small, isolated colonies; aerial mycelium white to pale yellow; reverse pale yellowish (2ca, 2ea); soluble pigment cream (1½ca).

Casein Agar—Growth moderate to good, pale yellow to tan (2ea, 3gc), slightly raised to raised, smooth to wrinkled, or occurring as isolated colonies, no aerial mycelium; reverse yellowish green (1½ia, 2ia); soluble pigment yellowish brown (3lc).

Bennett's Agar—Growth good, white, pale yellow, tan to brown (2ba, 3gc, 3ie), raised, or winkled, aerial mycelium white to pale yellow; reverse brown (3ic, 3le); soluble pigment yellowish (2ia).

Emerson's Agar—Growth moderate to good, pale yellowish to tan (2ea, 3gc), slightly raised to raised, slightly roughened to wrinkled, no aerial mycelium; reverse yellowish brown (2lc, 3lc); soluble pigment yellowish brown (3lc).

Nutrient Agar—Growth moderate, white, cream to pale yellow (2ca, 2ba), slightly raised; occurring as isolated, small colonies; aerial mycelium white to pale yellow; reverse pale greenish yellow (1½ea); no soluble pigment.

Gelatin Agar—Growth good, white to cream (1½ca), moderately raised, wrinkled, aerial mycelium white; reverse pale yellow (2ea); no soluble pigment.

Starch Agar—Growth good, white to cream (2ca), raised, roughened to wrinkled, aerial mycelium white; reverse yellowish to brown (2ga, 3ic); soluble pigment yellowish (2ga).

Potato Carrot Agar—Growth moderate, white to pale yellow (1ga, 2ba), slightly to moderately raised, smooth, or occurring as isolated colonies, aerial mycelium white to pale yellow; reverse pale yellow to grayish yellow (2ea, 2ic); soluble pigment cream (2ca).

Tap Water Agar—Growth poor to moderate, white to pale yellow (2ba), slightly raised, smooth; or occurring as small, isolated colonies; aerial mycelium white to pale yellow; reverse colorless to cream (2ca); no soluble pigment.

Culture N478-13 exhibited the following biochemical properties: melanin not produced; hydrogen sulfide not produced; gelatin liquefied; starch hydrolyzed; dextrose nitrate but not organic nitrate reduced to nitrite; poor growth on Jensen's cellulose but no growth on Levine and Schoenlein's cellulose; no decomposition on both cellulose broths; coagulation but no peptonization on milk; casein digestion positive; calcium malate digestion positive; tyrosine digestion weakly positive; glucose, fructose, mannitol, raffinose and sucrose utilized as a carbohydrate source; arabinose, inositol, rhamnose and xylose not utilized as a carbohydrate source.

When morphological observations were made after incubation for 15 days on oatmeal agar, culture N478-13 exhibited the following properties: spore mass in the yellow color-series; sporophores monopodially branched; spore chains strength, flexuous, curved, rarely hooked, 10 to 30 spores per spore chain; spores globose, oval, to elliptical, 0.8-1.0 μm in diam. or 1.0-1.4×0.7-1.0 μm, smooth or warty, as revealed by scanning electron microscopy.

The relationship of temperature to growth rate for culture N478-13 was as follows: 21° C., good growth; 28° C., good growth; 37° C., poor growth; 45° C., no growth.

On cell-wall analyses of culture N478-13 it was found that the whole-cell hydrolysates contained L,L-diaminopimelic acid, galactose and mannose.

Culture N478-13 is characterized by its pale yellow color of spores in mass, negative melanin reaction, straight to flexuous spore chains, and spores with a smooth or warty surface. It does not utilize arabinose, inositol, rhamnose, or xylose as a carbon source. Glucose, fructose, mannitol, raffinose, and sucrose support growth. These characteristics, distinguish it from all known species of Streptomyces of the yellow series. Jensen's cellulose is weakly utilized, but Levine and Schoenlein's cellulose is not utilized. Based on a combination of the physiological, biochemical, morphological and cultural properties, the culture N478-13 is considered a new species of Streptomyces and is name *Streptomyces routienii* Huang sp. nov. Culture N478-13 was deposited with the American Type Culture Collection, 12301 Parklawn Drive, Rockville, Md. 20852, U.S.A. under the provisions of the Rudapest Treaty on Sept. 14, 1983, under Accession No. ATCC 39446. The permanency of the deposit of culture N478-13 at the Americal Type Culture Collection is guaranteed throughout the effective life of any patent granted on this application; access to culture N478-13 is available during pendency of this application to the Commissioner of Patents and Trademarks under 35 USC 122 and 37 CFR 1.14; and all restrictions on the availability of the deposited culture will be removed irrevocably on the granting of a patent on this application.

The novel antibiotic substance of this invention is obtained by fermenting Streptomyces routienii Huang sp. nov., ATCC 39446, and extraction of the whole broth at a natural pH with methyl isobutyl ketone and concentration of the solvent. This affords a viscous oil which contains the new antibiotic substance of this invention, together with other antibiotic substances, including salinomycin and epi-17-deoxy-(0-8)-salinomycin. The viscous oil is suspended in heptane and batch treated with silica gel 60. The silica gel cake is eluted with chloroform, chloroform-ethyl acetate, ethyl acetate and ethyl acetate-acetone. After concentration, the ethyl acetate fraction yields a small amount of crude product from which the new antibiotic of this invention is isolated after repeated chromatography of the mixed sodium-potassium salt.

Streptomyces routienii, ATCC 39446, can be grown from 24° to 36° C. under submerged conditions with agitation and aeration on media consisting of carbohydrate sources such as sugars, starches, glycerol; organic nitrogen substances such as soybean meal, casamino acids, yeast extract; growth substance such as grain solubles, fish meal, cotton seed meal; mineral salts containing trace elements such as iron, cobalt, copper, zinc and calcium carbonate or phosphates as buffering agents. The antibiotic can be recovered by extracting the whole broth with various organic solvents such as n-butanol, methylisobutyl ketone, or chloroform at pH ranges from 4.0 to 8.0, or separating the mycelium after growth has been completed and extracting the mycelium, the filtrate being discarded.

Inoculum is prepared by scraping vegetative cells from slants or Roux bottles inoculated with Streptomyces routienii. A solid medium suitable for initial growth on slants and Roux bottles as ATCC medium No. 172.

| ATCC 172 | |
|---|---|
| Ingredient | Amount (gms./liter) |
| Glucose | 10 |
| Soluble Starch | 20 |
| Yeast Extract | 5 |
| NZ Amine A (Humko)* | 5 |
| Calcium Carbonate | 1 |
| Distilled Water to 1000 ml.; pH to 7.0 with KOH | |
| Add Agar | 20 |

*A purified enzymatic digest of casein.

Vegetative cells from slants are used to inoculate either shake flasks or inoculum tanks; or alternately the inoculum tanks are inoculated from shake flasks. In shake flasks, growth will generally have reached its maximum in 72 to 96 hours, whereas in the inoculum tanks growth will usually be at the most favorable period in 48 to 72 hours after inoculation. A fermentor is inoculated with vegetative broth from the inoculum flask or tank under completely aseptic conditions, and fermented for a period of 96 to 144 hours. Aeration is maintained in the shake flask by agitation on a shaker or in tanks by forcing sterile air through a sparger at the rate of ½ to 2 volumes of air per volume of broth per minute. The speed of agitation (stirring) depends upon the type of agitator employed; a shake flask is usually run at 150 to 200 cycles per minute and a fermentor at 300 to 1700 revolutions per minute. Sterility is maintained at all times. The temperature is regulated between 28° C. and 36° C. Foaming during the fermentation can be controlled with sterile antifoam such as refined soybean oil, or other suitable antifoam agents in the makeup and as needed aseptically after inoculation.

Shake flasks are prepared using one of the following media:

| CL13MZ | | JDYTT | |
|---|---|---|---|
| Ingredient | Grams/liter | Ingredient | Grams/liter |
| Glucose | 20 | Cerelose | 10 |
| Soy Flour | 10 | Corn Starch | 5 |
| NZ Amine YTT* | 5 | Corn Steep Liquor | 5 |
| Sodium Sulfate | 0.5 | NZ Amine YTT* | 5 |
| Cobalt Chloride | 0.002 | Cobalt Chloride | 0.002 |
| Calcium Carbonate | 2 | Calcium Carbonate | 3 |
| Water to 1 liter; pH 6.9–7.0 | | Water to 1 liter; pH 6.9–7.0 | |

*An enzymatic digest of casein.

One hundred milliliters of medium is distributed into 300 ml shake flasks and sterilized at 120° C. and 15 p.s.i. for 30 minutes. After cooling, the medium is inoculated with a vegetative cell suspension from Streptomyces routienii grown on ATCC 172 medium in agar. The flasks are shaken at 28° C. on a rotary shaker having a displacement of 1½ to 2½ inches and 150 to 200 cycles per minute (CPM) for three to four days. One flask is used to inoculate a five liter fermentation vessel containing three liters of one of the following media:

| CN-2 | | JDYTT | |
|---|---|---|---|
| Ingredient | Grams/liter | Ingredient | Grams/liter |
| Cerelose | 10 | Cerelose | 10 |
| Corn Starch | 10 | Corn Starch | 5 |
| Soybean Flour | 10 | Corn Steep Liquor | 5 |
| NZ Amine YTT | 10 | Cobalt Chloride | 0.002 |
| Cobalt Chloride | 0.002 | NZ Amine YTT | 5 |
| Calcium Carbonate | 1 | Calcium Carbonate | 3 |
| Water to 1 liter; pH 6.9–7.0 | | Water to 1 liter; pH 6.9–7.0 | |

One milliliter of L61 silicone is added as an antifoaming agent, then the vessels are sealed and sterilized at 120° C. and 15 p.s.i. for 45 minutes. The pots are inoculated with one (ca 3% inoculum) flasks, fermented for 96 to 144 hours at 30° C., stirred at 1700 revolutions per minute (RPM) with an air rate of one volume of air per volume of liquid per minute. When the fermentation is complete (based on an antibiotic disc assay against B. subtilis ATCC 6633) the fermentors are stopped, filtered at the natural pH with the aid of a filter aide such as Celite. The filter cake is slurried in methanol, concentrated in vacuo, diluted with 2-3 volumes of water, then extracted twice with ⅓ to ½ volume of methylisobutyl ketone or n-butanol. The solvent layer is separated from the aqueous phase by aspiration or centrifugation, sparkled, and concentrated in vacuo to a viscous oil.

The progress of antibiotic production during fermentation, and the bioactivity of the fermentation broth and recovery streams, can be monitored by biological assay of the broth employing a sensitive strain of Straphylococcus aureus or Bacillus subtilis. S. aureus ATCC 6538 and B. subtilis ATCC 6633 are suitable strains for this purpose. The components in the broth and recovery streams can be visualized by thin-layer chromatography (tlc) using Analtech silica gel GF plates in ethyl acetate. The developed plates are sprayed with vanillin reagent (3 g vanillin in 75 ml ethanol and 25 ml 85% phosphoric acid) and heated to 80° C. The antibiotic of this invention appears as a pale pink spot. The developed tlc plate can also be overlayed with agar seeded with either *S. aureus* or *B. subtilis* to which tetrazolium dye has been added and incubated at 37° C. for 16 hours to visualize the antibiotic (white against a pink background). The antibiotic can also be visualized by viewing the tlc plate under light of wavelength of 254 or 366 millimicrons under which the compound appears as a blue fluorescent spot.

Scale-up in large fermentors is carried out by preparing shake flasks containing 0.7 liters of CL13MZ or JDYTT medium. The shake flask inoculum is fermented for 3 to 5 days at 28° C., and used to inoculate a 50 or 1700 gallon fermentor containing 25 or 1200 gallons of JDYTT medium. Approximately one liter of inoculum is used in the tank. The fermentor, after running 5 to 7 days, is harvested (ca. 25 or 1100 gallons). The whole broth is extracted with 1/5 volume of methyl isobutyl ketone at natural pH, separated on an α DeLaval separator or a Podbielnack extractor and the solvent concentrated in vacuo to an oil.

The antibiotic compound of this invention of formula I is acidic, and it will form base salts. All such salts are within the scope of this invention. These salts are prepared by conventional methods for polyether (ionophore) antibiotics. In one method, a solution of the compound of formula I in a volatile, water immiscible, organic solvent is washed with an aqueous solution containing at least a stoichiometric equivalent, and preferably a large excess, of an appropriate basic agent. After drying the organic solvent solution, it is evaporated in vacuo to give the desired salt. Typical basic agents which can be used for this purpose include alkali metal hydroxides, such as sodium hydroxide and potassium hydroxide, alkaline earth metal hydroxides, such as calcium hydroxide and barium hydroxide, and ammonium hydroxide.

As indicated hereinbefore, the new antibiotic substance of this invention possesses antibacterial activity against a variety of gram-positive bacteria, such as *Staphylococcus aureus, Staphylococcus epidermidis, Streptococcus faecalis, Streptococcus pyogenes* and *Streptococcus pneumoniae*. This makes the compound of formula I, and its salts, useful for sanitary purposes, such as the washing of hands and the sterilization of hospital surfaces and equipment.

Furthermore, the antibiotic compound of formula I possesses activity against *Treponema hyodysenteriae*, a microorganism which causes dysentery in swine. Accordingly, the antibiotic substance of this invention of formula I is useful for controlling swine dysentery. For this purpose, the compound of formula I can be administered to swine alone, or, preferably, in a pharmaceutical composition in which the compound of formula I is mixed with a pharmaceutically-acceptable carrier or diluent.

Said pharmaceutical composition is prepared according to standard procedures for a veterinary antibiotic. For example, capsules can be prepared by filling gelatin capsules with the compound of formula I, suitably diluted with an inert diluent such as glucose, lactose, sucrose, starch or cellulose. Tablets can be prepared in conventional fashion, for example, by compressing a mixture of the compound of formula I, a diluent such as lactose or starch, a binding agent such as gelatin or guar gum, and a lubricant such as magnesium stearate or paraffin wax. Also, the compound of formula I can be administered orally in the form of elixers, syrups, solutions and suspensions. Solutions and suspensions can be aqueous, non-aqueous or partially aqueous. For parenteral administration, sterile, aqueous solutions are preferred. Parenteral administration includes intramuscular, intraperitoneal, subcutaneous and intravenous use. For intravenous use, the total concentration of solutes should be controlled to render the preparation isotonic.

The proportional ratio of the compound of formula I to the pharmaceutically-acceptable carrier will depend on the dosage contemplated and the route of administration; howver, said proportional ratio will normally be in the range from 1:10 to 2:1, especially 1:5 to 1:1.

Also, when using the compound of formula I to control swine dysentery, it is convenient to administer the compound by mixing it into the animal's feed. In this case, the compound of formula I will be added to the animal's feed at a level which will provide the appropriate daily dosage of the compound of formula I.

The prescribing veterinarian will ultimately decide the dosage of the compound of formula I which will be administered to combat swine dysentery, and this dosage will vary according to the route of administration and the severity of the animal's symptoms. However, the compound I will normally be administered orally at dosages in the range from 20 to 50 milligrams per kilogram of body weight per day and 10 to 30 milligrams per kilogram of body weight per day, usually in divided doses. In some instances, it may be necessary to use dosages outside these ranges.

Yet further, the antibiotic of formula I of this invention and the pharmaceutically-acceptable base salts thereof increase the efficiency of food utilization in poultry and ruminants, i.e. they act as growth promotants. The mechanism for utilization of the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle-upon-Tyne, England, 1970, pp. 408–410. The relative efficiency of VFA utilization is discussed by McCullough in "Feedstuffs", June 19, 1971, page 19; Eskeland et al. in J. An. Sci. 33, 282 (1971); and Church et al. in "Digestive Physiology and Nutrition of Ruminants," Vol. 2, 1971, pp. 622 and 625. Although acetates and butyrates are utilized, propionates are utilized with greater efficiency. A beneficial compound, therefore, stimulates animals to produce a higher proportion of propionates from carbohydrates, thereby increasing carbohydrate utilization efficiency.

The value of animal feeds generally has been determined directly by feeding the animal. British Pat. No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated calf which is fed on a commercial fattening ration plus hay. The rumen fluid is immediately filtered through cheese cloth, and 10 ml added to a 50 ml conical flask containing 400 mg of standard substrate (68% corn starch + 17% cellulose + 15% extracted soybean meal), 10 ml of a pH 6.8 buffer and the test compound. The flasks are gassed with oxygen free nitrogen for about two minutes, and incubated in a shaking water bath at 39° C. for about 16 hours. All tests are conducted in triplicate. After incubation, 5 ml of the sample is mixed with 1 ml of 25% metaphosphoric acid. After 10 minutes 0.25 ml of formic acid is added and the mixture centrifuged at 1,500 r.p.m. for 10 minutes. Samples are then analyzed by gas-liquid chromatography by the method of D. W. Kellog, J. Dairy Science, 52, 1690 (1969). Peak heights for acetic, propionic and butyric acids are determined for samples from untreated and treated incubation flasks.

When tested by the above in vitro technique, the antibiotic compound of formula I produced a 39% increase in propionic acid production at a dosage level of 10 parts per million, an increase of 20% at 5 parts per million, and an increase of 17% at 2.5 parts per million.

Accordingly the antibiotic of formula I, or a pharmaceutically acceptable base salt thereof will be used to increase the efficiency of food utilization in poultry and ruminants by incorporating said antibiotic or salt in the feed of the swine or ruminant at a level in the range from 5 to 50 parts per million.

The following example is provided solely for further illustration.

EXAMPLE

Isolation of Compound I (CP-61,405)

The whole broth (200 gallons) from a fermentation of the microorganism Streptomyces routienii Huang sp. nov., ATCC 39446, was extracted with methyl isobutyl ketone (100 gallons) and the methyl isobutyl ketone was evaporated in vacuo to give 183 g of a dark oil.

The dark oil was added to a suspension of 150 g of chromatographic grade silica gel in chloroform. The resulting mixture was stirred until the oil was evenly dispersed, and then 1.0 liter of heptane was added and the slurry was placed on top of 550 g of chromatographic grade silica gel in a 2 liter, coarse sintered-glass funnel. The solvents were allowed to flow by gravity and the residue was eluted further, as follows: 1 liter of heptane, 1 liter of heptane/chloroform (1:1), 4 liters of chloroform and 8 liters of chloroform/acetone (5:1). All the antibiotic activity was found in the chloroform/acetone fraction, which was then concentrated in vacuo to give 72.8 g of an oil.

The 72.8 g of oil was dissolved in ethyl acetate, 50 g of activated carbon was added, and the mixture was heated to the boiling point of the solvent. The mixture was filtered and the pale yellow filtrate was dispersed on 150 g of chromatographic grade silica gel. The solvent was removed by evaporation in vacuo and the residue was slurried in heptane. The resulting mixture was added to the top of 550 g of chromatographic grade silica gel in a coarse sintered-glass funnel, and then it was eluted as follows: 1 liter of heptane, 1 liter of heptane/chloroform (1:1), 2 liters of chloroform, 1 liter of chloroform/ethyl acetate (3:1), 6 liters of chloroform/ethyl acetate (1:1) and 2 liters of ethyl acetate. The chloroform/ethyl acetate and the ethyl acetate eluates were combined and evaporated in vacuo. The residue was dissolved in ethyl acetate/heptane, whereupon a solid precipitated. The solid (epi-17-deoxy-(0-8)-salinomycin) was collected by filtration and discarded. The filtrate was concentrated in vacuo to give the antibiotic I (CP-61,405), together with salinomycin and certain analogs thereof.

The latter material was purified by repeated column chromatography on silica gel using gradient elutions: chloroform to chloroform/acetone (4:1); heptane to ethyl acetate; and toluene to toluene/methanol (20:1). This afforded material which was crystallized from ethyl acetate/heptane as a mixed salt (560 mg). The mixed salt was dried at 60° C. for 3 hours under vacuum to give a solid which melted at 320°–321° C.

The mixed salt was dissolved in a mixture of chloroform and water, and the pH was lowered to 3.0 using phosphoric acid. The phases were separated and the chloroform phase was evaporated in vacuo to give the free acid, which was recrystallized from ethyl acetate/heptane.

The sodium salt was prepared from the free acid by dissolving the acid in chloroform and shaking with a saturated solution of sodium carbonate. The chloroform solution was separated, dried with anhydrous sodium sulfate and evaporated to an oil which crystallized from ethyl acetate-heptane. The crystals were collected by filtration and dried in vacuo, m.p. 334°–5° C.

The sodium salt exhibited the following properties:
Infrared Spectrum: Major absorptions at 2.9, 3.2, 3.5, 6.1, 6.2, 6.4, 6.65, 7.3, 7.45, 8.15, 9.15 and 12.5 microns.

Ultraviolet Spectrum: $E_1\ _{cm}^{1\%}$ (CH$_3$OH): 287 (258 nm); 400 (308 nm). $E_1\ _{cm}^{1\%}$ (CH$_3$OH/HCl): 277 (258 nm); 247 (269 nm); 331 (290 nm). $E_1\ _{cm}^{1\%}$ (CH$_3$OH/NaOH): 247 (254 nm); 356 (310 nm).

Analysis: Calcd. for $C_{26}H_{29}N_2O_7Na$: C, 61.77; H, 5.98; N, 5.54%. Found: C, 62.25; H, 5.80; N, 5.69%.

What is claimed is:

1. A process for producing the antibiotic of the formula

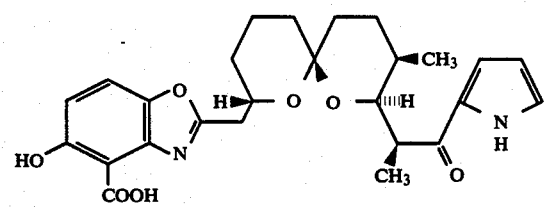

or a pharmaceutically-acceptable base salt thereof, which comprises cultivating the microorganism Streptomyces routienii Huang sp. nov. ATCC 39446 in an aqueous culture medium, containing an assimilable source of carbon, nitrogen and inorganic salts, under submerged, aerobic fermentation conditions, until a recoverable amount of said antibiotic, or a pharmaceutically-acceptable base salt thereof, is obtained.

* * * * *